United States Patent [19]

Merger et al.

[11]  4,202,199

[45]  May 13, 1980

[54] MANUFACTURE OF ALKYLPHENOL COMPOUNDS

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 839,775

[22] Filed: Oct. 6, 1977

[30] Foreign Application Priority Data

Nov. 6, 1976 [DE] Fed. Rep. of Germany ....... 2650888

[51] Int. Cl.$^2$ .............................................. C07C 37/14
[52] U.S. Cl. ................... 568/793; 568/744; 568/788
[58] Field of Search ........... 260/624 R, 624 C, 619 R; 568/780, 793, 788, 744

[56] References Cited

U.S. PATENT DOCUMENTS

| | | | |
|---|---|---|---|
| 2,802,884 | 8/1957 | D'Alelio | 260/624 |
| 3,037,052 | 5/1962 | Bortnick | 260/485 |

*Primary Examiner*—Werren B. Lone
*Attorney, Agent, or Firm*—Keil & Witherspoon

[57] ABSTRACT

Alkylphenol compounds are manufactured by continuous reaction of phenolic compounds with olefins in the presence of a pulverulent polystyrenesulfonic acid exchanger suspended in the reaction mixture. The products are starting materials for the manufacture of dyes, pesticides, pharmaceuticals, emulsifiers, dispersing agents, stabilizers, antioxidants, plasticizers, corrosion inhibitors, disinfectants, seed dressings, aging inhibitors, crop protection agents and scents.

11 Claims, No Drawings

MANUFACTURE OF ALKYLPHENOL COMPOUNDS

The present invention relates to a process for the manufacture of alkylphenol compounds by continuous reaction of phenolic compounds with olefins in the presence of a pulverulent polystyrene-sulfonic acid exchanger suspended in the reaction mixture.

Houben-Weyl, Methoden der Organischen Chemie, Volume 1/1, pages 585–587 discloses the use of cation exchangers, including sulfonated resins, as catalysts for continuous processes, and points out that the particle size of the resin has a substantial effect on its catalytic activity. Following Houben-Weyl, the particle diameter is therefore advantageously chosen to be from 0.5 to 1 mm for batchwise catalytic reactions. In contrast, continuous processes carried out in industrial columns require particularly coarse material to allow free passage of the reactants. Similarly, U.S. Pat. No. 2,802,884 discloses that the continuous alkylation of phenol with alkenes is carried out using only coarse sulfonic acid resin exchangers of from 10 to 20 mesh; the catalyst forms a fixed bed in the reactor.

German Published Application No. DAS 1,443,346 also discloses a continuous reaction carried out using a fixed bed of a porous, acid cation exchange resin, the greater part of the reaction mixture formed being recycled and the remainder being subjected to a renewed reaction in a further reactor packed with a fixed bed of the same catalyst. The description shows that the catalyst is always packed into a fixed bed; the use of fine pulverulent exchange resins in suspension is not mentioned.

All these processes are unsatisfactory in respect of yield and simplicity and economy of operation, and especially in respect of the removal of the large amounts of heat of reaction.

Our copending U.S. patent application Ser. No. 695,427 discloses a process for the continuous manufacture of a p-alkylphenol of the formula

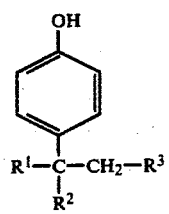

where $R^1$, $R^2$ and $R^3$ are identical or different and each is alkyl, $R^1$ may also be alkylphenyl or phenyl, and $R^2$ and/or $R^3$ may also be hydrogen, by reacting a phenol with an olefin in the presence of a cation exchanger, wherein phenol is reacted continuously with an olefin of the formula

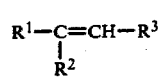

where $R^1$, $R^2$ and $R^3$ have the above meanings, in the presence of an organic cation exchanger possessing sulfonic acid groups and having a particle size of from 10 to 200 micrometers, the exchanger being suspended in the liquid reaction mixture.

We have found that the process of the said Application can be carried out advantageously, and can be generalized to form a process for the continuous manufacture of alkylphenol compounds of the formula

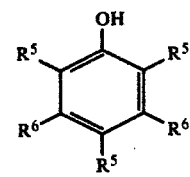

where at least one $R^5$ is

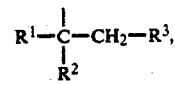

where $R^1$, $R^2$ and $R^3$ are identical or different and each is alkyl, $R^1$ may also be alkylphenyl or phenyl, and $R^2$ and/or $R^3$ may also be hydrogen, one or two $R^5$ may alternatively be hydrogen or an aliphatic, araliphatic or aromatic radical, and the individual radicals $R^6$ are identical or different and each is hydrogen or an aliphatic, araliphatic or aromatic radical, and one of the radicals $R^5$ and $R^6$ may alternatively be —$OR^4$, where $R^4$ is hydrogen or an aliphatic radical, and the radicals $R^6$ may also each, provided they are in the o-position or p-position to a radical —$OR^4$, be

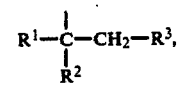

where $R^1$, $R^2$ and $R^3$ have the above meanings, but in total at least one of the radicals $R^5$ and $R^6$ is —$OR^4$ or an aliphatic, araliphatic or aromatic radical, if the starting compounds used are phenolic compounds of the formula

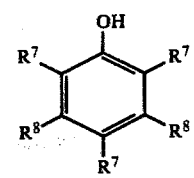

where the radicals $R^7$ and/or $R^8$ are each hydrogen if the corresponding radicals $R^5$ and/or $R^6$ are

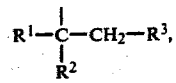

whilst if $R^5$ and $R^6$ have other meanings $R^7$ has the same meaning as the particular $R^5$ and $R^8$ has the same meaning as the particular $R^6$.

Where o-cresol and isobutylene are used, the reaction may be represented by the following equation:

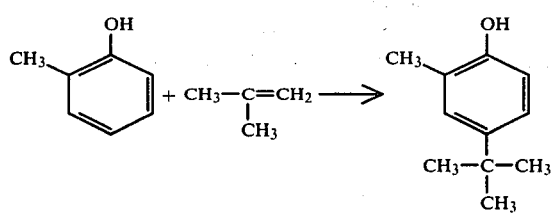

Compared to the conventional processes, the process of the invention surprisingly gives a large number of alkylphenol compounds more simply and more economically, with better space-time yield and in higher purity, particularly on an industrial scale and in continuous operation. The heat of reaction is removed more efficiently and special cooling devices, and recycling of the greater part of the reaction mixture, are unnecessary. Conventional reactor jacket cooling or pipe coil cooling suffices. Since lower reaction temperatures can be used, the life of the catalyst is also longer, and hence the process is more economical. Compared to the disclosure in the above German Published Application, the process according to the invention permits the use of lower and hence substantially more advantageous catalyst factors, the catalyst factor being defined as $$\frac{\text{dry catalyst (g)}}{\text{feed rate (g/hour)}}$$

The reaction itself takes place relatively more rapidly, particularly below 120° C. All these advantages of the process of the invention are surprising, especially in view of the fact that not only macro-reticular but also, advantageously, gel-like exchanger resins are used. Regarding the macro-reticular or gel-like structure of resins, reference may be made to German Pat. No. 1,168,908. Using the fine pulverulent exchanger resins according to the invention in continuous operation, poorer yields, lower throughput of the reaction mixture inadequate removal of the heat of reaction, accompanied with substantial formation of decomposition products and polymerization, would also have been expected, particularly in view of the disclosure in Houben-Weyl. Furthermore, it is surprising that the catalyst can be removed without the addition of filtration aids.

The invention is based, inter alia, on the observation that catalyst particles having a size of from 10 to 200 micrometers can be suspended in the continuously flowing reaction mixture, by means of a stirrer or mixer, in such a way that they can be retained on a reactor filter unit, and be back-mixed, without forming an impermeable membrane on the filter. It does not require the use of any specific type of filter to achieve this advantage, and the losses of catalyst particles are very low. Surprisingly, the process of the invention can be operated for very long periods. Problems due to film formation on the filters only arise if the mixer fails and can, where necessary, be dealt with by passing inert gas in countercurrent through the filter.

The starting material II can be reacted with the phenolic compound III in the stoichiometric amount or in excess, preferably in a ratio of from 0.3 to 1, especially from 0.5 to 0.75, mole of starting material II per mole of phenolic compound III. The end products I with the alkyl group in the o-position or, especially, in the p-position to the hydroxyl group or alkoxy group are formed preferentially. If a larger excess of starting material II, especially 1.5 moles or more, advantageously from 1.5 to 3.5 moles, of starting material II per mole of phenolic compound III is used, increasing amounts of o,p- and/or o,o',p-alkylphenols or, in the case of dihydroxybenzenes, increasing amounts of alkylphenol compounds I which are trialkylated and/or dialkylated in the orthopositions and/or para-positions to each of the two hydroxyl groups on the nucleus, are formed, to an extent corresponding to the amount of starting material II. Thus, by using an appropriate excess of starting material II, 2,6- and 2,5-dialkyl compounds I can be obtained from 1,4-hydroxy compounds III (hydroquinones) or 1,4-alkoxy compounds III, 2,4,6-trialkyl compounds I, 2,4-dialkyl compounds I and, to a greater degree, 4,6-dialkyl compounds I can be obtained from 1,3-hydroxy compounds III (resorcinols) or 1,3-alkoxy compounds, and 3,4,6 (or 3,5,6) -trialkyl compounds I and, to a greater degree, 3,5(or 4,6)-dialkyl compounds I can be obtained from 1,2-hydroxy compounds III (pyrocatechols) or 1,2-alkoxy compounds III. Correspondingly substituted end products I are obtained, as a rule, if the starting compound III already possesses other radicals, in place of hydrogen atoms, at one or more of the above positions of the nucleus.

Preferred starting materials II and III and accordingly preferred end products I are those where $R^1$, $R^2$ and $R^3$ are identical or different and each is alkyl of 1 to 9, especially of 1 to 4, carbon atoms, $R^1$ may also be alkylphenyl or phenylalkyl of 7 to 12 carbon atoms or phenyl, and $R^2$ and/or $R^3$ may be hydrogen, all three $R^5$ or, advantageously, two $R^5$ or especially one $R^5$ is

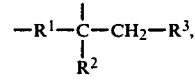

where $R^1$, $R^2$ and $R^3$ have the above meanings, one or two $R^5$ may also be hydrogen, alkyl of 1 to 9, especially of 1 to 4, carbon atoms, alkylphenyl or phenylalkyl of 7 to 12 carbon atoms or phenyl, the individual radicals $R^6$ may be identical or different and each is hydrogen, alkyl of 1 to 9, especially of 1 to 4, carbon atoms, alkylphenyl or phenylalkyl of 7 to 12 carbon atoms or phenyl, one of the radicals $R^5$ and $R^6$ may also be —$OR^4$, where $R^4$ is hydrogen or alkyl of 1 to 9, especially of 1 to 4, carbon atoms, the radicals $R^6$ may also each, where they are in the o-position or p-position to a radical -$OR^4$, be

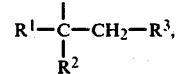

where $R^1$, $R^2$ and $R^3$ have the above meanings, but in total at least one of the radicals $R^5$ and $R^6$ is —$OR^4$ or alkyl of 1 to 9, especially of 1 to 4, carbon atoms, alkylphenyl or phenylalkyl of 7 to 12 carbon atoms or phenyl, and the radicals $R^7$ and/or $R^8$ are each hydrogen if the corresponding radicals $R^5$ and/or $R^6$ are

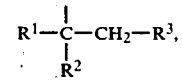

whilst if $R^5$ and $R^6$ have other meanings, $R^7$ has the same meaning as the particular $R^5$ and $R^8$ has the same meaning as the particular $R^6$. The above radicals may in addition be substituted by groups which are inert under the reaction conditions, e.g. alkyl of 1 to 3 carbon atoms. The use of branched alkenes is preferred. In contrast to the conventional processes, mixtures of alkenes, or of alkenes with alkanes, such as are formed, for example, on cracking or dehydrogenating hydrocarbons, e.g. petroleum, or on oligomerizing olefins, especially isobutylene, propylene or n-butene, or hydrogenating carbon monxide, may also be used advantageously.

Examples of olefins which may be used as starting materials II are 1-n-pentene, 1-n-hexene, 1-n-heptene, 1-n-octene, 1-n-nonene, 1-n-decene, 1-n-undecene, 1-n-dodecene, propene and 1-n-butene, the above alkenes substituted in the 2-, 3- or 4-position by methyl, ethyl, n-propyl, isopropyl, n-butyl, isobutyl, sec.-butyl or tert.-butyl, 2,3-dimethyl-n-butene, 3,3-dimethyl-n-butene, 2,5-dimethylheptene, 3,3-dimethylheptene, 2,34-trimethylheptene, 2,4-dimethylheptene, 2,3-dimethylheptene, 4,4-dimethylheptene, 2,3-diethylhexene, 4,4-dimethylhexene, 2,3-dimethylhexene, 2,3-dimethylhexene, 2,5-dimethylhexene, 3,3--dimethylhexene, 3,4-dimethylhexene, 2-methyl-3-ethylpentene, 3-methyl-3-ethylpentene, 2,3,3-trimethylheptene, 2,4,4-trimethylpentene, 2,3,3-trimethylpentene, 2,3,4-trimethylpentene and 2,3,3,4-tetramethylpentene, analogous alkenes with the double bond in the 2-position or 3-position in the molecule, branched alkenes such as are obtained as mixtures on dimerizing isobutylene or n-butene (octenes) or trimerizing isobutylene or n-butene (dodecenes) or propylene (nonenes) or tetramerizing propylene (dodecenes), styrene, o-methylstyrene, m-methylstyrene, p-methylstyrene, 3,4-dimethylstyrene, 2,4-dimethylstyrene, 2,5-dimethylstyrene, o-ethylstyrene, m-ethylstyrene, p-ethylstyrene, 3,4-diethylstyrene, m-propylstyrene, p-propylstyrene, m-isopropylstyrene, p-isopropylstyrene, m-butylstyrene, p-butylstyrene, m-isobutylstyrene, p-isobutylstyrene, p-sec.-butylstyrene and p-tert.-butylstyrene.

The following are preferred: isobutylene, diisobutylene, triisobutylene, styrene, α-methylstyrene, nonenes and dodecenes formed by trimerizing or tetramerizing propylene, 2,3-dimethyl-1-butene, 2-methyl-1-butene, 2-methyl-2-butene, 2-methyl-1-pentene, 2-methyl-1-hexene, 2-methyl-1-heptene, 2,3-dimethyl-1-pentene, 2,3-dimethyl-1-hexene and 2,4,4-trimethyl-1-pentene.

Examples of suitable phenolic compounds III are o-methyl-, o-ethyl-, o-propyl-, o-isopropyl-, o-butyl-, o-isobutyl-, o-sec.-butyl-, o-tert.-butyl, o-benzyl- and o-phenylphenol, m-methyl-, m-ethyl-, m-propyl-, m-isopropyl-, m-butyl-, m-isobutyl-, m-sec.-butyl-, m-tert.-butyl, m-benzyl- and m-phenylphenol, p-methyl-, p-ethyl-, p-propyl-, p-isopropyl-, p-butyl-, p-isobutyl-, p-sec.-butyl-, p-tert.-butyl-, p-benzyl- and p-phenyl-phenol, dimethyl-, diethyl-, dipropyl-, diisopropyl-, dibutyl-, diisobutyl-, di-sec.-butyl-, di-tert.-butyl-, dibenzyl- and diphenyl-phenol with the two substituents in the 2,3-position, 2,4-position, 3,4-position, 3,5-position, 2,5-position or 2,6-position to the hydroxyl group; trimethyl-, triethyl-, tripropyl- and tributyl-phenol with the 3 substituents in the 2,3,4-position, 3,4,5-position, 2,3,6-position or 2,3,5-position to the hydroxyl group; hydroquinone, resorcinol and pyrocatechol which are unsubstituted or are monosubstituted or disubstituted in the 2-, 3-, 4-, 5- and/or 6-position by the above substituents, and corresponding unsubstituted or substituted monemethyl, monoethyl, monopropyl, monoisopropyl, monobutyl, monoisobutyl, monopentyl, monohexyl, monoheptyl, monooctyl and monononyl ethers. Preferred compounds are o-methyl-, o-ethyl-, o-isopropyl-, m-methyl-, m-ethyl-, p-methyl-, p-ethyl-, p-isopropyl-, p-tert.-butyl-, p-pentyl-, p-hexyl-, p-octyl-, p-nonyl- and p-benzylphenol, dimethyl- and diethyl-phenol with the two substituents in the 2,4-, 2,6- and 3,5-position to the hydroxyl group, 2,3,5- and 2,3,6-trimethyl-phenol, hydroquinone, resorcinol, pyrocatechol, 2-methylhydroquinone and the corresponding monomethyl ethers.

The reaction is in general carried out continuously at from 70° to 140° C., preferably from 80° to 125° C., especially from 80° to 120° C., under reduced pressure, superatmospheric pressure or atmospheric pressure, preferably under a pressure of from 1 to 10 bars and especially of from 1 to 3 bars. The residence time is preferably from 0.5 to 20, especially from 1 to 10, hours and the throughput is from 1 to 120, especially from 5 to 50, kilograms of starting material II per kilogram of catalyst per hour.

The catalysts used are organic cation exchangers containing sulfonic acid groups, advantageously resins consisting of sulfonated styrenedivinylbenzene copolymers and other sulfonated cross-linked styrene polymers, and phenol-formaldehyde or benzene-formaldehyde resins containing sulfonic acid groups. The use of sulfonated styrene-divinylbenzene copolymer exchangers is preferred. The exchangers are in the acid form, and not in the form of salts. The catalyst has a particle size of from 10 to 200, preferably from 20 to 180, especially from 25 to 150, micrometers and advantageously has a gel-like structure. Examples of suitable exchanger resins are those marketed under the description ®LEWASORB A-10. It is also possible to mill commercial resins, for example ®Amberlit IR-120, ®Dowex 50, ®Lewatit S-100, ®Nalcite HCR, ®Permutit RS and ®Wofatit KPS-200 to the particle size according to the invention and then use them. Advantageously, they are dehydrated in the conventional manner, e.g. by heating under reduced pressure, before use. However, they can also be dehydrated by displacing the water with hydrophilic organic liquids and then heating the resin at 100° C. under reduced pressure, or by azeotropic distillation with an organic liquid.

During the reaction, the catalyst is in suspension, as a rule in the reaction mixture which is being formed. Advantageously, a part of the liquid phenolic compound III or of the starting mixture of phenolic compound III and olefin II is taken and the catalyst is suspended in the liquid with thorough mixing. Advantageously, no additional solvent is used, but under certain circumstances, for example in order to lower the viscosity of the reaction mixture, solvents which are inert under the reaction conditions may be employed. Examples of suitable solvents are aliphatic or cycloaliphatic hydrocarbons, e.g. heptane, nonane, gasoline fractions within a boiling point range of from 70° to 190° C., cyclohexane, methylcyclohexane, decalin, petroleum ether, hexane, naptha, 2,2,4-trimethylpentane, 2,2,3-trimethylpentane, 2,3,3-trimethylpentane and octane, halohydrocarbons, especially chlorohydrocarbons, e.g. tetrachloroethylene, 1,1,2,2-tetrachloroethane or 1,1,1,2-tetrachloroethane, dichloropropane, methylene chloride, dichlorobutane, chloroform, carbon tetrachloride, tetrachloroethane, 1,1,1-trichloroethane or 1,1,2- trichloroethane, trichloroethylene, pentachloroethane, cis-dichloroethylene, 1,2-dichloroethane and 1,1-dichloroethane, tetrahydrofuran, dioxane, and mixtures of the above. The solvent is advantageously used in an amount of from 10 to 1,000 percent by weight, preferably from 50 to 100 percent by weight, based on starting material II. In the case of mixtures of starting materials II, for example obtained by cracking petroleum, the saturated hydrocarbons present in the mixture may serve as solvents for the suspension. The amount of initially taken phenolic compound III or starting mixture and/or organic solvent is chosen so that the catalyst is present in suspension in the reaction mixture being formed in an amount of from 0.3 to 10, preferably form 1 to 3, percent by weight, based on the weight of the total liquid mixture in the reaction space. Advantageously, the reaction mixture is mixed throughout the reaction, preferably by stirring at a rate of at least 300, advantageously from 400 to 2,000, especially from 500 to 1,000, revolutions per minute. Where mixing devices without stirrers are used, for example when mixing by means of an inert gas such as nitrogen, devices which introduce shearing energy corresponding to the above rate of stirring are preferred. This results in a finely dispersed suspension. Provided the above mixing conditions are observed, a wide range of conventional stirring devices can be used, namely injectors, ball jets, vortex jets, turbine stirrers, mixing nozzles, Lechler mixing nozzles, paddle stirrers, anchor stirrers, bar-type stirrers, propeller stirrers, Cramer stirrers, vibromixers, finger-type stirrers, crossbeam stirrers, gyratory stirrers, grid stirrers, flat stirrers, spiral turbines, scoop stirrers, planetary stirrers, centrifugal gyratory stirrers, rotating atomizers, ejectors, triangular stirrers, hollow stirrers, tubular stirrers and impeller stirrers. It is also possible to use apparatus and equipment, such as stirred kettles, stirred kettle cascades, flow tubes, air-lift type stirring units, homogenizing equipment, gyratory mixers, turbomixers, emulsifying centrifuges, ultrasonic tubes, flow mixers, rotating drums, chamber reactors, circulatory reactors, loop reactors, cellular reactors, screw reactors, bubble columns, jet scrubbers, liquid ring pumps, ejector-type tubular reactors and thin film reactors; if only for economic reasons stirred kettles are preferred.

The reaction may be carried out as follows: a liquid mixture of the starting material II, the phenolic compound III and the solvent, if any, is passed, at the reaction temperature and under the reaction pressure, through a suspension of the catalyst in the starting mixture or reaction mixture and is filtered. The end product is then isolated from the reaction mixture in the conventional manner, for example by distillation. The filtration advantageously takes place before the suspension leaves the reactor. Suitable filters are acid-resistant filter cloths, wire gauze filters and sintered metal filters, provided the mesh widths or pore diameters are smaller than the catalyst particles. Decanting equipment can also be used advantageously for separating off the catalyst.

The alkylphenol compounds I which may be manufactured by the process of the invention are valuable starting materials for the manufacture of dyes, pesticides, pharmaceuticals, emulsifiers, dispersing agents, stabilizers, antioxidants, plasticizers, corrosion inhibitors, disinfectants, seed dressings, aging inhibitors, crop protection agents and scents. Regarding their use, reference may be made to the above publications, to Ullmanns Encyklopädie der technischen Chemie, Volume 13, pages 440–447 and to Kirk-Othmer, Encyclopedia of Chemical Technology, Volume 1, pages 901–916 (2nd edition).

In the examples which follow, parts are by weight.

EXAMPLE 1

A suspension of 124 parts of 4-hydroxyanisole and 3 parts of exchanger resin is prepared in a stirred reactor by stirring at 500 revolutions per minute at 100° C. under 1 bar, and 28 parts of isobutene are passed in. The exchanger resin is a sulfonated styrene-divinylbenzene copolymer resin which has been dehydrated for 20 hours at 100° C. under reduced pressure before being used; it has a gel structure and a particle size for from 20 to 150 micrometers. The suspension in the reactor is now stirred steadily at 500 revolutions per minute. After one hour, 80 parts of 4-hydroxyanisole and 20 parts of isobutene are fed in hourly, and correspondingly 100 parts of suspension are filtered through a suction take-off line fitted with a metal filter (pore diameter 10 micrometers) and are fed to a fractional distillation. After 100 hours' operation, 5,486 parts (85% of theory, based on starting material II) of a mixture of 2-tert.butyl-4-hydroxyanisole and 3-tert.-butyl-4-hydroxyanisole of boiling point 140°–145° C./14 millibars are obtained in addition to 490 parts (6% of theory, based on starting material II) of 2,5-di-tert.-butyl-4-hydroxyanisole. The conversion is 51 percent, based on 4-hydroxyanisole employed. The isobutene is consumed quantitatively.

EXAMPLE 2

A suspension of 110 parts of pyrocatechol and 3 parts of exchanger resin is prepared in a stirred reactor by stirring at 500 revolutions per minute at 110° C. under 1 bar, and 30 parts of isobutene are passed in. The exchanger resin is a sulfonated styrene-divinylbenzene copolymer resin which has been dehydrated for 20 hours at 100° C. under reduced pressure before being used; it has a gel structure and a particle size of from 20 to 100 micrometers. The suspension in the reactor is now stirred steadily at 500 revolutions per minute. After one hour, 135 parts of pyrocatechol and 40 parts of isobutene are fed in hourly, and correspondingly 175 parts of suspension are filtered through a suction take-off line fitted with a metal filter (pore diameter 10 micrometers) and are fed to a fractional distillation. After 100 hours' operation, 10,790 parts (91% of theory, based on starting material II) of 4-tert.-butylpyrocatechol of boiling point 151°–152° C./15 millibars are obtained in addition to 390 parts (4.9% of theory, based on starting material II) of di-tert.-butylpyrocatechol. The conversion is 55 percent, based on pyrocatechol employed. The isobutene is consumed virtually quantitatively.

EXAMPLE 3

A suspension of 110 parts of p-cresol and 5 parts of exchanger resin is prepared in a stirred reactor by stirring at 500 revolutions per minute at 100° C. under 1 bar, and 60 parts of isobutene are passed in. The exchanger resin is a sulfonated styrene-divinylbenzene copolymer resin which has been dehydrated for 20 hours at 100° C. under reduced pressure before being used; it has a gel structure and a particle size of from 20 to 100 micrometers. The suspension in the reactor is now stirred steadily at 500 revolutions per minute. After one hour, 100 parts of p-cresol and 50 parts of isobutene are fed in hourly, and correspondingly 150 parts of suspension are filtered through a suction take-off line fitted with a metal filter (pore diameter 10 micrometers) and are fed to a fractional distillation. After 100 hours' operation, 13,020 parts (89% of theory, based on starting material II) of 2-tert.-butyl-4-methylphenol of boiling point 115°–117° C./13 millibars are obtained in addition to 1,005 parts (10% of theory, based on starting material II) of 2,6-di-tert.-butyl-4-methylphenol. The conversion is 91 percent, based on p-cresol employed. The isobutene is consumed virtually quantitatively.

EXAMPLE 4

A suspension of 110 parts of p-cresol and 15 parts of exchanger resin is prepared in a stirred reactor by stirring at 500 revolutions per minute at 95° C. under 1 bar, and 100 parts of isobutene are passed in. The exchanger resin is a sulfonated styrene-divinylbenzene copolymer resin which has been dehydrated for 20 hours at 100° C. under reduced pressure before being used; it has a gel structure and a particle size of from 20 to 200 micrometers. The suspension in the reactor is now stirred steadily at 500 revolutions per minute. After 2 hours, 65 parts of p-cresol and 60 parts of isobutene are fed in hourly, and correspondingly 126 parts of suspension are filtered through a suction take-off line fitted with a metal filter (pore diameter 10 micrometers) and are fed to a fractional distillation. After 100 hours' operation, 10,340 parts (87% of theory, based on starting material II) of 2,6-di-tert.butyl-4-methylphenol of boiling point 131°–132° C./14 millibars are obtained in addition to 1,970 parts (11% of theory, based on starting material II) of 2-tert.-butyl-4 methylphenol. The conversion is 98% of theory, based on p-cresol employed. The isobutene is consumed virtually quantitatively.

EXAMPLE 5

A suspension of 110 parts of resorcinol and 4 parts of exchanger resin is prepared in a stirred reactor by stirring at 500 revolutions per minute at 100° C. under 1 bar, and 30 parts of isobutene are passed in. The exchanger resin is a sulfonated styrene-divinylbenzene copolymer resin which has been dehydrated for 20 hours at 100° C. under reduced pressure before being used; it has a gel structure and a particle size of from 20 to 150 micrometers. The suspension in the reactor is now stirred at 500 revolutions per minute. After 2 hours, 135 parts of resorcinol and 40 parts of isobutene are fed in hourly at 100° C. under 1 bar, and correspondingly 175 parts of suspension are filtered through a suction take-off line fitted with a metal filter (pore diameter 10 micrometers) and are fed to a fractional distillation. After 100 hours' operation, 10,575 parts (89% of theory, based on starting material II) of 4-tert.-butyl-resorcinol of boiling point 134°–136° C./2 millibars are obtained in addition to 520 parts (6.5% of theory, based on starting material II) of di-tert.-butyl-resorcinol. The conversion is 54% of theory, based on resorcinol employed. The starting material II is consumed virtually quantitatively.

We claim:

1. A process for the continuous manufacture of alkylphenol compounds of the formula

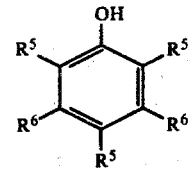

where $R^5$ and $R^6$ are defined as follows:

(A) at least one $R^5$ is

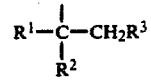

and one or two $R^5$ may also be hydrogen, alkyl of 1 to 9 carbon atoms, alkylphenyl of 7 to 12 carbon atoms, phenylalkyl of 7 to 12 carbon atoms or phenyl, (i) $R^1$, $R^2$ and $R^3$ are identical or different and each is alkyl of 1 to 9 carbon atoms with the proviso that $R^1$ may also be alkylphenyl of 7 to 12 carbon atoms, phenylalkyl of 7 to 12 carbon atoms or phenyl and at least one of $R^2$ and $R^3$ may be hydrogen, (B) $R^6$ may be identical or different and each is hydrogen, alkyl of 1 to 9 carbon atoms, alkylphenyl of 7 to 12 carbon atoms, phenylalkyl of 7 to 12 carbon atoms or phenyl, or (C) one of the radicals $R^5$ and $R^6$ may also be $-OR^4$ where $R^4$ is hydrogen or alkyl of 1 to 9 carbon atoms, (ii) when the radicals $R^6$ are located in the ortho- or para-position to an $-OR^4$ radical, said $R^6$ radicals may also each be

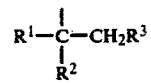

wherein $R^1$, $R^2$ and $R^3$ are defined as described in part (A) above, with the proviso that in the total of $R^5$ and $R^6$, at least one of said $R^5$ and $R^6$ radicals is selected from the group consisting of $-OR^4$, alkyl of 1 to 9 carbon atoms, alkylphenyl of 7 to 12 carbon atoms, phenylalkyl of 7 to 12 carbon atoms or phenyl, and $R^1$, $R^2$, $R^3$, $R^4$, $R^5$ and $R^6$ may also be substituted by alkyl of 1 to 3 carbon atoms, which comprises:

continuously reacting phenolic compounds of the formula

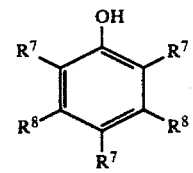

where the radicals $R^7$ and $R^8$ are each hydrogen when the corresponding radicals $R^5$ and $R^6$ in formula I are

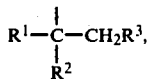

and when the radicals $R^5$ and $R^6$ have meanings other than

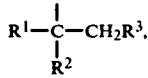

then $R^7$ has the same meaning as that particular $R^5$ and $R^8$ has the same meaning as that particular $R^6$, with olefins of the formula

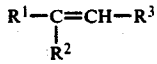  II.

where $R^1$, $R^2$ and $R^3$ are defined as in part (A) above, at temperatures of from 70° to 140° C. in the presence of an organic cation exchanger as a catalyst having a gel-like structure and possessing sulfonic acid groups, said exchanger having a particle size of from 10 to 200 micrometers and being suspended in the liquid reaction mixture.

2. The process of claim 1, in which the reaction is carried out with a ratio of from 0.3 to 1 mole of starting material II per mole of phenolic compound III.

3. The process of claim 1, in which the reaction is carried out with from 1.5 to 3.5 moles of starting material II per mole of phenolic compound III.

4. The process of claim 1, in which the reaction is carried out at from 80° to 125° C.

5. The process of claim 1, in which the reaction is carried out under a pressure of from 1 to 10 bars.

6. The process of claim 1, in which the reaction is carried out with a residence time of from 0.5 to 20 hours and a throughput of from 1 to 120 kilograms of starting material II per kilogram of catalyst per hour.

7. The process of claim 1, in which the reaction is carried out with resins consisting of sulfonated styrene-divinylbenzene copolymers, other sulfonated cross-linked styrene polymers and/or phenol-formaldehyde or benzene-formaldehyde resins containing sulfonic acid groups.

8. The process of claim 1, in which the reaction is carried out using an exchanger with a particle size of from 20 to 180 micrometers.

9. The process of claim 1, in which the reaction is carried out using an exchanger with a particle size of from 25 to 150 micrometers.

10. The process of claim 1, in which the reaction is carried out with the catalyst being present in the reaction mixture undergoing formation in an amount of from 0.3 to 10 percent by weight, based on the weight of the total liquid mixture in the reaction space.

11. The process of claim 1, in which the reaction is carried out whilst stirring at a rate of from 400 to 2,000 revolutions per minute.

* * * * *